Figure 1:
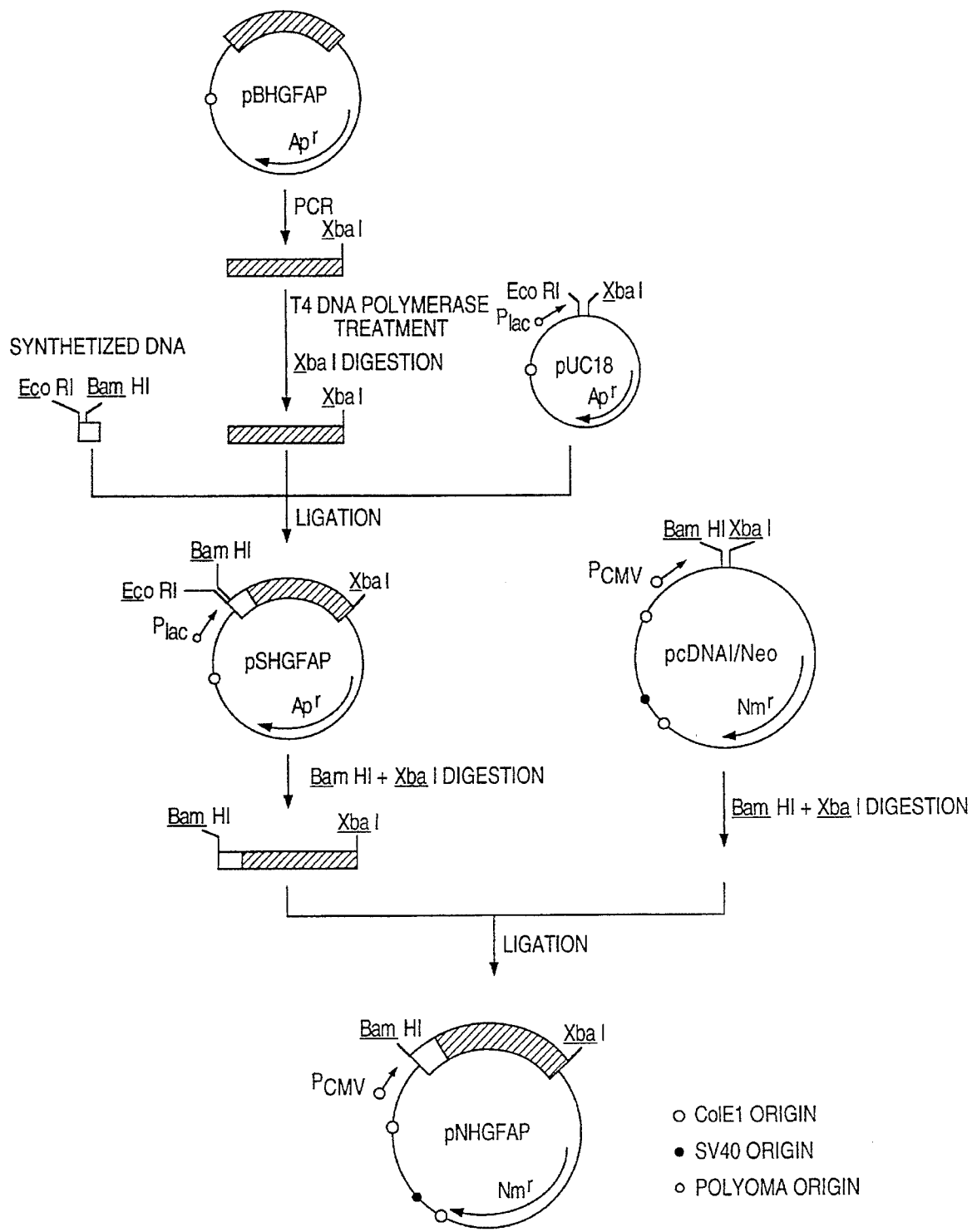

United States Patent [19]

Shimomura et al.

[11] Patent Number: 5,466,593
[45] Date of Patent: Nov. 14, 1995

[54] HEPATOCYTE GROWTH FACTOR ACTIVATING PROTEASE AND GENE ENCODING THE PROTEASE

[75] Inventors: Takeshi Shimomura, Machida; Kazunori Yamada, Yokohama; Yuuki Morimoto, Machida; Naomi Kitamura, Moriguchi; Keiji Miyazawa, Ashiya, all of Japan

[73] Assignee: Mitsubishi Kasei Corporation, Tokyo, Japan

[21] Appl. No.: 148,910

[22] Filed: Nov. 5, 1993

[30] Foreign Application Priority Data

Nov. 5, 1992 [JP] Japan .................................. 4-296133
Nov. 20, 1992 [JP] Japan .................................. 4-312234
Nov. 20, 1992 [JP] Japan .................................. 4-312242

[51] Int. Cl.[6] .................... C12N 15/57; C12N 15/63; C12N 5/10
[52] U.S. Cl. .................... 435/219; 435/226; 435/691; 435/240.1; 435/252.3; 435/254.11; 435/320.1; 435/172.3; 536/232; 935/14; 935/66
[58] Field of Search .................... 536/23.2; 435/69.1, 435/240.1, 252.3, 252.33, 320.1, 219–226

[56] References Cited

U.S. PATENT DOCUMENTS 4,740,461  4/1988  Kaufman .................................. 435/69.1

FOREIGN PATENT DOCUMENTS

0412557A1  2/1991  European Pat. Off. .

OTHER PUBLICATIONS

Patent Abstracts of Japan, vol. 17, No. 446, Aug. 17, 1993, & JP-A-05 103 670 (Mitsubishi Kasei Corp) Apr. 27, 1993.

Naka et al., "Activation of hepatocyte growth factor by proteolytic conversion of a single chain form to a heterodimer", Journal of Biological Chemistry, vol. 267, No. 28, pp. 20114–20119, Oct. 5, 1992.

Cytotechnology, "A Novel Protease Obtained from FBS–Containing Culture Supernatant, that Processes Single Chain form Hepatocyte Growth Factor to two Chain form in Serum–Free Culture" Shimomura et al., 8:219–229 (1992).

Journal of Biological Chemistry, "Molecular Cloning and Sequence Analysis of the cDNA for a Human Serine Protease Responsible for Activation of Hepatocyte Growth Factor" Miyazawa et al., vol. 268, No. 14, May 15, 1993, pp. 10024–10028.

Journal of Biological Chemistry, "Activation of the Zymogen of Hepatocyte Growth Factor Activator by Thrombin" Shimomura et al., vol. 268, No. 30, Oct. 25, 1993, pp. 22927–22932.

*Primary Examiner*—Robert A. Wax
*Assistant Examiner*—Gabriele Bugaisky
*Attorney, Agent, or Firm*—Wenderoth, Lind & Ponack

[57] ABSTRACT

A gene encoding a protease derived from human serum and having an activity to convert single-chain hepatocyte growth factor (HGF) into active two-chain HGF and a method of producing the protease by the use of said gene are provided. A method of producing a precursor protein of said protease is also provided.

12 Claims, 2 Drawing Sheets

HEPATOCYTE GROWTH FACTOR ACTIVATING PROTEASE AND GENE ENCODING THE PROTEASE

The present invention relates to a novel protein, a gene encoding the protein, a transformant comprising the gene, and a method for producing the protein with the use of the transformant. More specifically, the present invention relates to a novel 36 kDa protein having a protease activity which converts inactive single-chain hepatocyte growth factor (HGF) into active two-chain HGF by cleaving the inactive HGF at a specific site, a gene encoding the protein, a transformant comprising the gene, and a method for producing the protein with the use of the transformant. The present invention also relates to 96 kDa precursor of the protein, a gene encoding the precursor, a transformant comprising the gene, and a method for producing the precursor with the use of the transformant.

It is known through in vitro experiments that a single-chain human HGF does not have physiological activities but two-chain human HGF has these activities. It is also known that most human HGFs produced by a gene recombinant technique with the use of a serum-free culture are the inactive single-chain form. A method for producing HGF with the use of a serum-free culture has been considered preferable because the addition of serum to culture is expensive.

Some of the inventors of the present invention previously discovered a protein in mammalian serum that converts single-chain HGF into two-chain HGF. They also found that the protein had a molecular weight of about 34,000 dalton as determined by SDS polyacrylamide gel electrophoresis (Japanese Patent Publication (Kokai) No. 5-103670). However, it requires considerable labor to obtain a purified product of the protein, because the protein exists in a very small amount in serum. Further, the protein in an active form is unstable in serum.

As a result of the inventors' research to overcome the above disadvantages and to readily provide a protein having an equivalent activity to the above-mentioned protein, the inventors of the present invention eventually obtained a gene encoding the protein, and found that the protein can be produced on a large scale by the use of a gene engineering technique.

Further, the inventors attempted to purify, from human plasma, a precursor of the protein having the protease activity, which converts inactive single-chain HGF into active two-chain HGF.

As a result, the inventors have discovered two novel precursor proteins having molecular weights of about 34,000 dalton and about 96,000 dalton as determined by SDS polyacrylamide gel electrophoresis. A mouse antibody against the active protease existing in human serum reacts with the precursor proteins. By treatment with a serine protease, the two precursor proteins are processed to obtain the active protein of this invention having a molecular weight of about 34,000 dalton and having the above-mentioned protease activity.

Further, as the result of inventors' research to readily provide proteins having equivalent properties as the above-mentioned precursor proteins, the inventors eventually obtained a gene encoding the precursor protein, and found that the proteins can be produced on a large scale by the use of a gene engineering technique.

Thus, the present invention provides a protein characterized by the amino acid sequence of SEQ ID NO: 1, a gene encoding the protein, a vector that can be used to express a polypeptide encoded by the gene, a transformant including the vector, and a method for producing the protein with the use of the transformant.

Further, the present invention provides novel protein characterized by the following physical and chemical properties:

(i) the molecular weights of two precursor proteins are about 96,000 dalton and 34,000 dalton as determined by SDS polyacrylamide gel electrophoresis; and (ii) by treatment with a serine protease, the precursor proteins are processed into a 34,000 dalton protein having a protease activity which specifically cleaves the human hepatocyte growth factor consisting of 728 amino acid residues at a site between arginine at the 494th position, and valine at the 495th position counting from the amino terminal.

The present invention also provides a protein characterized by the amino acid sequence of SEQ ID NO: 12, a gene encoding the protein, a vector that can be used to express a polypeptide encoded by the gene, a transformant including the vector, and a method for producing the protein with the use of the transformant.

The present invention is further illustrated below.

In the accompanying drawings:

FIG. 1 shows the construction scheme for an expression vector for the production of the protein having the protease activity of the present invention, wherein $P_{lac}$ represents a *E. coli* lac promoter, $P_{CMV}$ represents a cytomegalovirus (CMV) promoter, $Ap^r$ represents an ampicillin resistance gene, $Nm^r$ represents a neomycin resistance gene.

Figure 2:
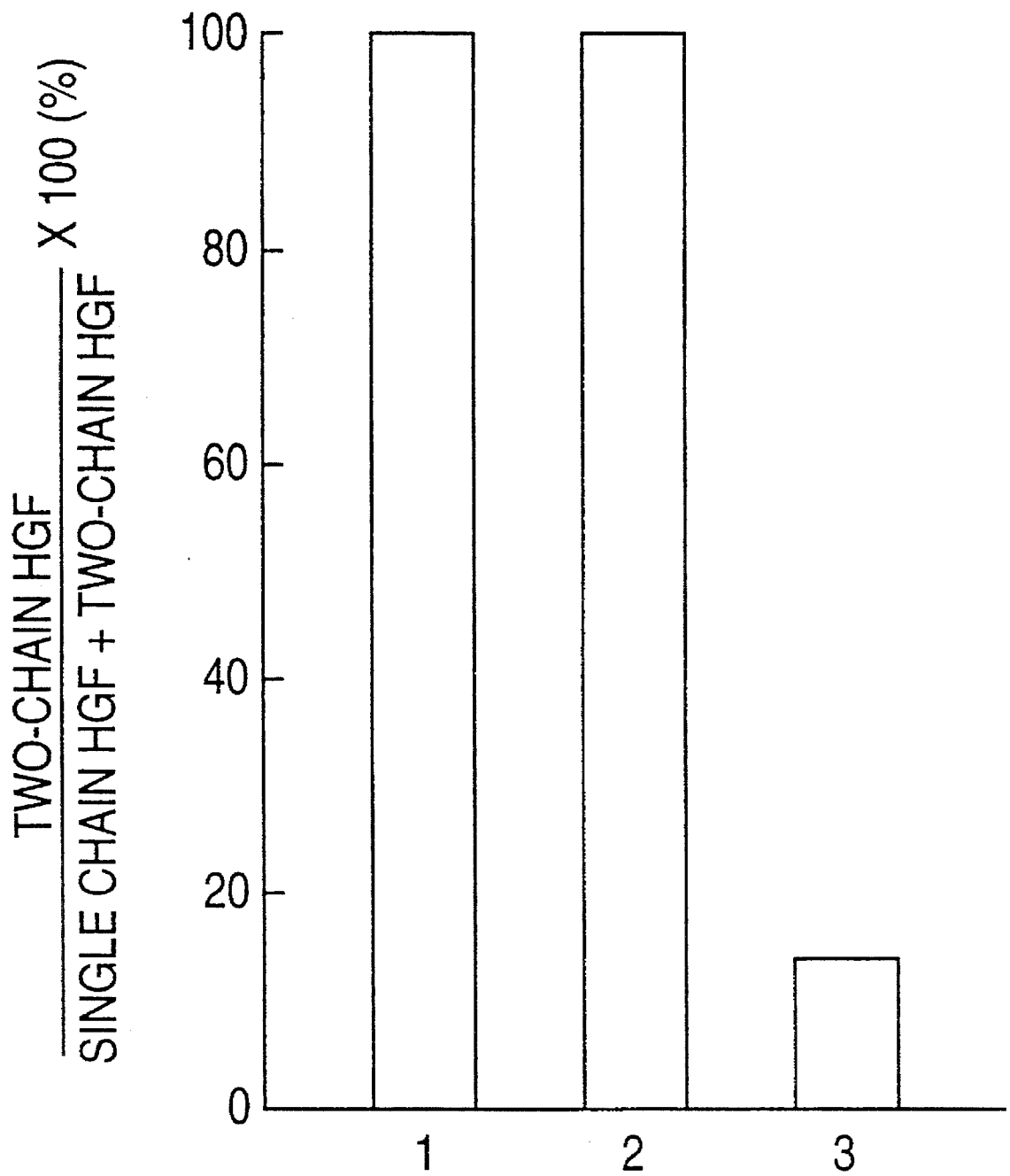

FIG. 2 presents a bar graph showing the rate of the production of two-chain HGF and single-chain HGF in the presence or absence of the precursor proteins activated by thrombin of the present invention, wherein 1 represents the experimental result in the presence of about 100 ng/ml of the precursor protein having a molecular weight of about 96,000 dalton, 2 represents the result in the presence of about 100 ng/ml of the precursor protein having a molecular weight of about 34,000 dalton, and 3 represents the result in the absence of the precursor proteins.

The novel protein having the protease activity of the present invention (hereinafter, sometimes referred to as "the protein having the protease activity") includes a protein having the amino acid sequence of SEQ ID NO: 1 and variants thereof having the same protease activity obtained by a deletion, replacement, modification, or addition of a part of amino acids of the protein having the sequence of SEQ ID NO: 1.

Examples of a gene encoding the above-mentioned protein having the protease activity include a gene comprising the base sequence of SEQ ID NO: 2 as a part of the gene and a gene represented by the base sequence of SEQ ID NO: 3.

A DNA fragment including such gene can be obtained as described below. As for a cDNA library including DNA encoding the protein having the protease activity of the present invention, a commercially available cDNA library prepared from human liver can be used. Phagemids from the library are used to infect cells as described by Saito et al., (Proc. Natl. Acad. Sci. USA, 83, 8664–8668 (1986)) and the infected cells are cultured. Colonies obtained after culturing are screened by the colony hybridization method ("Molecular Cloning", Cold Spring Harbor Laboratory 320–328 (1982)) with the use of partial DNA fragments or DNA fragments having base sequences that correspond to partial amino acid sequences of the protein of the present invention as probes and desired DNA fragments can be obtained.

As for probes used in the colony hybridization method, DNA fragments which include parts of the gene encoding the protein having the protease activity of the present invention and which are prepared by the polymerase chain reaction (PCR) method (Science, 239, 487–491 (1988)) can be used. In more detail, PCR is carried out with the use of the DNA fragment of SEQ ID NO: 4 (corresponding to a part of the amino acid sequence of SEQ ID NO: 6) as a plus (+) strand DNA primer and the DNA fragment of SEQ ID NO: 5 (corresponding to a part of the amino acid sequence of SEQ ID NO: 7) as a minus (−) strand DNA primer and the resulting DNA fragment of SEQ ID NO: 2 is used as a probe. Synthetic oligonucleotides based on DNA sequences deduced from the amino acid sequence of the protein of the present invention can also be used as probes.

DNAs are then prepared from positive colonies by the method of T. Maniatis et al. ("Molecular Cloning", Cold Spring Harbor Laboratory, 85 (1982)). The resulting DNAs are digested with an appropriate restriction enzyme, e.g., BamHI, cloned in a plasmid, e.g., pUC18 or the like, and sequenced by the dideoxy method of Sanger et al. (Proc. Natl. Acad. Sci. USA, 74, 5463 (1977)), thereby the base sequences of the desired DNA fragments can be determined.

The base sequences of the DNA fragments thus determined (for example, the sequences comprising the base sequence of SEQ ID NO: 2 as a part and the base sequence of SEQ ID NO: 3) encode the protein of the present invention of SEQ ID NO: 1. The DNA fragments of the present invention also include variants of the DNA fragments encoding the protein as long as variant-encoded polypeptides have a protease activity to convert single-chain HGF into two-chain HGF. Such variants are prepared by a deletion, replacement, modification, and addition of a part of the bases.

Each of the DNA fragments so obtained is modified at their 5' terminal, inserted into downstream of a promoter in an expression vector, and introduced into a host cell, for example, *E. coli, Bacillus subtilis,* yeast, or an animal cell.

A method for producing the protein of the present invention is illustrated in detail below. Preferably, an expression vector including a promoter at an appropriate site to transcript the DNA fragment encoding the protein of the present invention is used. For example, when a host cell is derived from microorganisms, such as *E. coli, Bacillus subtilis,* an expression vector comprising a promoter, ribosome binding (SD) sequence, the gene encoding the protein, transcription termination sequence, and a gene regulating the promoter is preferable.

Examples of promoters used in the present invention include promoters derived from *E. coli*, phages or the like, such as promoter of tryptophan synthase (trp); lambda phage $P_L$ and $P_R$; and $P_{25}$ and $P_{26}$ promoters, which are promoters of early gene of $T_5$ phage. Promoters which are modified or designed artificially, such as pac promoter (Agric. Biol. Chem., 52, 983–988 (1988)) are also useful.

As for ribosome binding sequences, sequences derived from *E. coli*, phage or the like as well as synthetic sequences which include a consensus sequence having contiguous four or more bases of a sequence complimentary to a sequence at a 3' terminal region of 16S ribosome RNA can be used. Transcription termination sequences are not critical, but preferably, an expression vector includes lipoprotein terminator, trp operon terminator, or the like.

Further, it is preferable that an expression vector includes the above-mentioned sequences, a promoter, a SD sequence, the gene encoding the protein, and a transcription termination sequence in this order from 5' upstream. An expression vector including multiple units of SD sequence and the gene in the same orientation can also be used for increasing the number of the copies of transcriptional units in a vector (Japanese Patent Publication (Kokai) No. 1-95798). The method comprises a step of inserting into an expression vector.

Examples of expression vectors that can be used include pUA12 (Japanese Patent Publication (Kokai) No. 1-95798), commercially available pKK233-2 (Pharmacia), and the like. Similarly, the expression vectors pGEX series (Pharmacia), which can express a desired protein as a fusion protein, are also useful. Standard methods for transforming host cells can be employed.

Transformants can be cultured according to the method described in "Molecular Cloning" (Cold Spring Harbor Laboratory, 1982).

As described above, host cells derived from microorganisms such as *E. coli, Bacillus subtilis,* yeast, and the like can be used, but animal cells, such as CHO cells, COS cells, mouse L cells, mouse C127 cells, mouse FM3A cells and the like are preferably used to express the gene encoding the protein, taking it into consideration that the activity of the protein of the present invention may be affected by the protein conformation and the sites of thiol bindings between many cysteine residues included in the protein.

Among known various promoters used for animal cells, SV40 promoter, promoter of the metallothionein gene and the like can be used. Under such promoter, a secretion signal and the gene encoding the protein are inserted according to the transcriptional orientation. A DNA fragment including two or three genes can also be inserted instead of a single gene. Two or three units of the gene and a promoter at its 5' side can be combined together and inserted into an expression vector according to the transcriptional orientation.

It is preferable that the gene encoding the protein is followed by a polyadenylation site downstream of the gene. For example, one of the polyadenylation sites derived from SV40 DNA, β-globin gene, metallothionein gene, and the like is inserted downstream of the gene encoding the protein. When two to three units of the gene and a promoter at its 5' side are combined together, each of the gene in a unit can be followed by a polyadenylation site at its 3' side. Further, to attain a high level of expression, it is effective to insert genes derived from animal, such as SV40 gene, rabbit β-globin gene or the like; or splicing signal sequences, of intron or exon, synthesized chemically, into upstream or downstream of the gene encoding the protein.

It is preferable to use selection markers when animal cells, e.g., CHO cells, are transformed with the above mentioned expression vectors. With the use of an expression vector including selection marker gene downstream of a polyadenylation site in the same or reverse orientation, it is not necessary to cotransform a cell with additional plasmid including a selection marker gene. Examples of such selection marker genes include a DHFR gene which confers a cell a methotrexate resistance (J. Mol. Biol., 159, 601 (1982)); a Neogene which confers a cell an antibiotic G-418 resistance (J. Mol. Appl. Gene., 1, 327 (1982)); the Ecogpt gene derived from *E. coli* which confers a cell a mycophenolic acid resistance (Proc. Natl. Acad. Sci. USA, 78, 2072 (1981)); a hph gene which confers a cell an antibiotic hygromycin resistance (Mol. Cell. Biol., 5, 410 (1985)); and the like.

Each of these resistance genes is linked to a promoter, e.g., a promoter derived from SV40, at its 5' upstream and to a polyadenylation site at its 3' downstream. Commercially available expression vectors comprising a selection marker can be used. For example, pcDNA/Neo that comprises a neomycin resistance gene, can be used.

When an expression vector comprising the gene encoding the protein of the present invention does not have any selection markers, an additional vector comprising a selection marker, e.g., pSV2Neo (J. Mol. Appl. Genet., 1, 327 (1982)), pMBG (Nature, 294, 228 (1981)), pSV2gpt (Proc. Natl. Acad. Sci. USA, 78, 2072 (1981)), pAd-D26-1 (J. Mol. Biol., 159, 601 (1982)) can be used with the expression vector to cotransform a cell, thereby the resulting transformant can be selected readily by a phenotype.

It is preferable to repeat cotransformation of the cell including the gene encoding the protein with the use of various selection markers, because the expression level of the protein can be increased by a cotransformation.

An expression vector is introduced into an animal cell by the calcium phosphate precipitation method (Virology, 52, 456 (1973)), the electroporation method (J. Membr. Biol., 10, 279 (1972)), or the like.

Transformed animal cells can be cultured by the methods known to those of ordinary skill in the art, including a suspension culture and an adhesion culture. MEM medium, RPMI 1640 medium, and the like can be used and the cells are cultured in the presence of 5 to 10% serum or an appropriate growth factor, or in the absence of serum. The transformed animal cells producing the protein secrete the protein into a medium. Therefore, the protein can be separated and purified from the supernatant of the culture. In more detail, the supernatant of the culture including the produced protein can be purified by various chromatography methods, such as a chromatography method including a combination of two or more resins selected from anion exchange resin, heparin immobilized resin, hydrophobic chromatography resin, affinity chromatography resin, and the like to obtain isolated and purified protein.

The precursor proteins of the present invention are described below. The precursor proteins of the present invention can be obtained by the following purification steps. The precursor protein with the molecular weight of about 96,000 dalton can be derived from the plasma prepared by the steps of drawing blood from a normal individual (human), adding ethylenediaminetetraacetic acid (EDTA), benzamidine, 6-amino-n-caproic acid n-hexyl ester p-toluensulfonate, soybean trypsin inhibitor, 6-amidino-2-naphthyl p-guanidinobenzoate dimethanesulfonate (naphamostat mesilate), aprotinin or the like to inhibit the action of coagulation factors in the blood, and then removing the cells by centrifugation. After the plasma is diluted with water to two to five volumes, the diluted plasma is chromatographed by a Heparin-sepharose column (Pharmacia) or the like. The resulting fractions including the 96 kDa precursor protein are further chromatographed by a hydrophobic chromatography column (for example, with the use of Phenyl-sepharose column manufactured by Pharmacia). The fractions including the 96 kDa precursor protein are chromatographed by an antibody affinity chromatography column, thereby the 96 kDa precursor protein of the present invention can be obtained. This antibody affinity chromatography column is prepared by the steps of immunizing a mouse with the novel human protein described in Japanese Patent Publication (Kokai) No. 5-103670, fusing a single cell from the mouse spleen and a myeloma cell to obtain a hybridoma producing an antibody reactive with the immunized protein, and immobilizing the antibody onto appropriate resins according to a standard method.

The precursor protein with the molecular weight of about 34,000 dalton can be derived from the plasma prepared by the steps of drawing blood from a normal individual (human), and adding EDTA, 6-amino-n-caproic acid n-hexyl ester p-toluensulfonate, or the like. The plasma is chromatographed by a Heparin-sepharose column or the like in the same manner as described above. The resulting fractions including the precursor protein are chromatographed by a hydrophobic chromatography column or the like in the same manner as described above. The resulting fractions including the precursor protein are applied onto aprotinin immobilized affinity column (Pentafirm) and unbounded fractions are chromatographed by the above-mentioned antibody affinity column, thereby the precursor protein can be obtained. Optionally, a step of purifying the proteins of the present invention includes an ion exchange column chromatography, a gel filtration chromatography, a hydroxyapatite column chromatography, or the like.

The molecular weights of the purified precursor proteins of the present invention are about 96,000 dalton and about 34,000 dalton determined by SDS polyacrylamide gel electrophoresis. They are processed to have the similar activity as that of the human protein described in Japanese Patent Publication (Kokai) No. 5-103670 by the treatment with a serine protease such as thrombin. One of the precursor proteins of the present invention includes the amino acid sequence of SEQ ID NO: 11 as a part of the protein. One of the precursor proteins of the present invention include the amino acid sequence of SEQ ID NO: 12 as a part of the protein. Also included in the scope of the present invention are variants of the precursor proteins prepared by a deletion, replacement, modification, or addition of a part of the amino acid sequences of the precursor proteins.

Examples of the genes encoding the precursor proteins include a gene comprising the base sequence of SEQ ID NO: 13 as a part of the gene, a gene represented by the base sequence of SEQ ID NO: 14, and the like.

A DNA fragment including such gene can be obtained by the same method for obtaining the protein having a protease activity as described above.

As for probes used in the colony hybridization method, DNA fragments that include parts of the gene encoding the precursor proteins and that prepared by the PCR method can be used. For example, PCR is carried out with the use of the DNA fragment of SEQ ID NO: 4 as a plus (+) strand DNA primer and the DNA fragment of SEQ ID NO: 5 as a minus (−) strand DNA primer and the resulting DNA fragment of SEQ ID NO: 13 is used as a probe. Synthetic oligonucleotides based on DNA sequences deduced from the amino acid sequence of the precursor proteins of the present invention can also be used as probes.

Further, DNAs are prepared from positive colonies and the base sequences of the desired DNA fragments can be determined by the method described above.

The base sequences of the DNA fragments thus determined (for example, the sequences comprising the base sequence of SEQ ID NO: 13 as a part and the base sequence of SEQ ID NO: 14) encode the precursor proteins of the present invention. The DNA fragments of the present invention also include variants of the DNA fragments encoding the precursor proteins as long as variant-encoded polypeptides acquire a protease activity to convert single-chain HGF into two-chain HGF, after the polypeptides are processed. Such variants are prepared by a deletion, replacement, modification, and addition of a part of the bases.

Each of the DNA fragments so obtained is modified at their 5' terminal, inserted downstream of a promoter in an expression vector, and introduced into a host cell, for example, E. coli, Bacillus subtilis, yeast, or an animal cell by a standard method.

Production of the precursor proteins of the present invention may be conducted in a similar manner to the method for producing the protein having a protease activity described above.

The present invention is further illustrated by the following examples. However, this invention is not limited to the following examples.

EXAMPLE 1

Purification of the Protein Having the Protease Activity and Determination of Partial Amino Acid Sequence of the Same A protein having molecular weight of about 34,000 as determined by SDS polyacrylamide gel electrophoresis was purified from human serum by the method described in Example 2 in Japanese Patent Publication (Kokai) No. 5-103670, said protein having a protease activity to convert single-chain HGF into two-chain HGF. The purified protein was allowed to react in Buffer A (6M guanidine hydrochloride, 0.002M EDTA, and 1M Tris-HCl buffer, pH 8.5) with 2-mercaptoethanol at 4° C. for 2 hours to reduce the protein. Monoiodoacetic acid at the same concentration as that of the protein was added to the resulting reaction solution and the mixture was allowed to react in the presence of nitrogen gas at room temperature for one hour in the darkness for carboxymethylation of the protein. The resulting reaction mixture was applied to the YMC pack C4 column (YMC). The column was then eluted with a linear gradient of 10% to 70% acetonitrile/isopropyl alcohol (3/7) for 30 minutes, and the fractions including the main peak were collected.

The pooled fractions were mixed with 0.1% ammonium bicarbonate solution including 2M urea, and allowed to react with TPCK-trypsin (MILES Laboratory) or TLCK-chimotrypsin (MILES Laboratory) in a ratio of enzyme:substrate= 1:50 at 37° C. for 16 hours. The resulting reaction mixture was applied to high pressure liquid chromatography (HPLC). The column was then eluted with a linear gradient of 0% to 80% in acetonitrile/isopropyl alcohol (3/7) for 1 hour, and multiple peptide fragments were obtained.

The peptide fragments were dried under reduced pressure, dissolved in 60 µl of 50% trifluoroacetic acid, added to a glass filter treated with polybrene, and the amino acid sequence thereof was determined by $470A Sequencer (Applied Biosystems) employing Edman degradation. The identification of each phenylthiohydantoin (PTH) amino acid was performed with the use of MCI gel ODS IHU (0.46×15 cm) column (Mitsubishi Kasei Corp.). The column was eluted with acetate buffer (10 mM acetate buffer, pH4.7, 0.01% SDS, and 38% acetonitrile) at a flow rate of 1.2 ml/min, at 43° C., and a PTH-amino acid was detected by 269 nm absorbance. Among these peptides, two amino acid sequences are shown in SEQ ID NO: 6 and 7.

EXAMPLE 2

Preparation of DNA Fragments Including Parts of the Gene Encoding the Protein Having the Protease Activity by the PCR Method Commercially available human liver cDNA bank (Quickclone™ human liver cDNA, Clonetech) was used as a template DNA. PCR was performed by Perkin Elmer Cetus DNA Thermal Cycler with the use of Gene Amp DNA Amplification Reagent Kit (Takara Shuzo Co. Ltd.). First, 100 µl of reaction mixture was prepared including a template DNA (1 ng), 10 µl of x10 reaction buffer (500 mM KCl, 100 mM Tris-HCl buffer, pH8.3, 15 mM $MgCl_2$, and 0.1% (w/v) gelatin), 2 µl each of 10 mM dGTP, dATP, dCTP, and dTTP, 0.1 µl of (+) strand DNA primer of SEQ ID NO: 4 as primer #1, 0.1 µl of (−) strand DNA primer of SEQ ID NO: 5 as primer #2 to make final concentration of 0.1 µM, 0.5 µl of Taq DNA polymerase, and sterilized deionized water. Template DNA was then amplified by 30 cycles of the PCR including pretreatment at 94° C. for 10 minutes, denaturation at 94° C. for 1 minute, annealing at 37° C. for 2 minutes, and extension at 72° C. for 3 minutes. The reaction was stopped by incubation at 72° C. for 7 minutes.

The resulting reaction mixture was extracted with phenol:chloroform=1:1, and ethanol precipitated. The precipitate was dissolved in 21.5 µl of sterilized deionized water. Then, 2.5 µl of x10 restriction enzyme buffer (50 mM Tris-HCl buffer, pH7.5, 10 mM $MgCl_2$, 100 mM KCl, and 1 mM DTT) and 1 µl of restriction enzyme BglII (15 units) were added to the solution and the resulting mixture was allowed to react at 37° C. for 2 hours. The reaction mixture was electrophoresed using 5% polyacrylamide gel electrophoresis, the 323 bp band was extracted from the gel by a standard technique to recover a DNA fragment, and the fragment was ethanol precipitated.

The DNA fragment was inserted into pUC19 vector at BamHI site and the base sequence thereof was identified according to a standard method. The base sequence of the identified DNA fragment prepared by PCR is shown in SEQ ID NO: 2.

EXAMPLE 3

Screening for a Clone Including a Complete Gene Encoding the Protein Having the Protease Activity The fragment with 323 bp prepared as described in Example 2 was labeled with $^{32}P$ according to the method described in "Molecular Cloning" (Cold Spring Harbor Laboratory, 1982) and used as a probe for screening. The library to be screened was Premade Lambda Phage Library (Stratagene), which was a human liver cDNA library derived from 49 years old male. *E. coli* XL1-Blue (Stratagene) was infected with the phage to make about 500 million plaques. The infected cells were cultured on NZY medium overnight and then transfered on Gene Screen Plus membranes (Dupont). The membranes were allowed to stand on paper filters soaked with 0.1M NaOH—0.5M NaCl for 2 minutes, and then on paper filters soaked with 1.5M NaCl—0.5M Tris-HCl buffer (pH7.5) for 5 minutes. The membranes were further treated two more times, washed with 2×SSC, and dried on a dried paper filter in the air. DNAs on the membranes were fixed with UV light at 120 $mJ/cm^2$.

Five membranes thus treated were soaked in 50 ml of solution including 50 mM Tris-HCl buffer, pH 7.5, 1M NaCl, and 1% SDS and allowed to stand at 65° C. for 2 hours. The membranes were hybridized in 40 ml of solution including 5 ng/ml probe labeled with P, 100 µg/ml salmon sperm DNA, 50 mM Tris-HCl buffer, pH 7.5, 1M NaCl, and 1% SDS at 65° C. for 16 hours. The membranes were then washed in 2×SSC at room temperature for 5 minutes, 0.1×SSC at room temperature for 30 minutes for two times, and autoradiographed by a standard method, thereby 40 positive clones were obtained.

EXAMPLES 4

Subcloning of DNA Fragments and Identification of the Base Sequences Thereof

Plasmids were prepared directly from positive phage clones obtained in Example 3 by the excision method. Phage was extracted from single plaque by the treatment with 500 μl of SM buffer (50 mM Tris-HCl buffer, pH 7.5, 100 mM NaCl, 10 mM MgSO$_4$, and 0.01% gelatin) and 20 μl of chloroform. The mixture including 200 μl of the above-mentioned phage extracted solution, 200 μl of XL1-Blue, and 1 μl of R408 helper phage was allowed to stand 37° C. for 15 minutes. Then, 5 ml of 2× YT medium was added to the mixture and the resulting solution was shake cultured at 37° C. for 3 hours. The culture was then heated to 70° C. for 20 minutes followed by centrifugation at 4000 g for 5 minutes to obtain a supernatant. The supernatant was diluted to make 100-fold diluted solution. Then 20 μl of the diluted solution was mixed with 200 μl of XL1-Blue and the mixture was allowed to react 37° C. for 15 minutes. Then 2 μl of the resulting mixture was plated onto a LB agarose medium including 40 μl/ml ampicillin. Twenty-four plasmids from the colonies appeared on the plate were obtained, and analyzed. The clone having the longest insert (pBHGFAP) was analyzed and the base sequence of the insert was identified. The base sequence thus determined is shown in SEQ ID NO: 3. Based on this base sequence, the amino acid sequence of the protein having a protease activity of the present invention was deduced (SEQ ID NO: 1).

EXAMPLE 5

Construction of an Expression Vector

FIG. 1 shows a construction of an expression vector including the gene encoding the protein having a protease activity of the present invention.

The plasmid pBHGFAP prepared in Example 3 was used as a template DNA and PCR was performed by Perkin Elmer Cetus DNA Thermal Cycler with the use of the Gene Amp DNA Amplification Reagent Kit (Takara Shuzo Co., Ltd.). First, 100 μl of reaction mixture was prepared including a template DNA (0.5 μg), 10 μl of x10 reaction buffer (500 mM KCl, 100 mM Tris-HCl buffer, pH8.3, 15 mM MgCl$_2$, and 0.1% (w/v) gelatin), 16 μl each of 1.25 mM dGTP, dATP, dCTP, and dTTP, 5 μl of (+) strand DNA primer of SEQ ID NO: 8 as primer #3, 5 μl of (−) strand DNA primer of SEQ ID NO: 9 as primer #4, 0.5 μl of Taq DNA polymerase, and sterilized deionized water. Template DNA was then amplified by 22 cycles of the PCR including pretreatment at 94° C. for 10 minutes, denaturation at 94° C. for 1 minute, annealing at 52° C. for 1.5 minutes, and extension at 72° C. for 2 minutes. The reaction was stopped by incubation at 72° C. for 7 minutes. The resulting reaction mixture was extracted with phenol:chloroform=1:1, and the amplified DNA was ethanol precipitated. The precipitate was dissolved in 16 μl of sterilized deionized water, and electrophoresed using 5% polyacrylamide gel. The 862 bp band was extracted from the gel by a standard technique to recover a DNA fragment and the DNA fragment was ethanol precipitated.

The DNA fragment thus obtained was blunt-ended by a standard method with the use of T4 DNA polymerase and then cleaved with XbaI. The cleaved DNA fragments were recovered again, and 15 ng of the DNA fragments was mixed with 5 ng of synthetic DNA of SEQ ID NO: 10 and 20 ng of a plasmid vector pUC18 cleaved with EcoRI and XbaI, and the mixture was allowed to ligate by the use of Ligation Kit (Takara Shuzo Co. Ltd.). The resulting plasmid was transformed into competent cells, E. coli JM105 (Competent High, Toyobo) according to the manufacturers instruction. The transformants thus obtained were screened by a standard method and the plasmid pSHGFAP including the desired 926 bp insert was obtained. The plasmid pSH-GFAP (8 μg) was cleaved with restriction enzymes BamHI and XbaI, treated with phenol/chloroform, and ethanol precipitated. The precipitate was dissolved in sterilized deionized water and electrophoresed using 5% polyacrylamide gel. The 920 bp band was extracted from the gel by a standard technique to recover a DNA fragment, which was then ethanol precipitated. Ten ng of the DNA fragment thus obtained and 5 ng of pcDNAI/Neo plasmid that was digested with BamHI and XbaI and treated with alkali phosphatase were ligated. The resulting plasmid was transformed into competent cells, E. coli DH5 (Competent High, Toyobo) according to the manufacturers instruction. The transformants thus obtained were screened by a standard method and the plasmid pNSHGFAP including the desired insert was obtained.

EXAMPLE 6

Expression of the Protein Having the Protease Activity in E. coli

E. coli comprising the plasmid pSHGFAP prepared in Example 5 was inoculated in 10 ml of LB medium containg 50 μg/ml ampicillin and cultured at 37° C. overnight (12 to 16 hours). Aliquot (0.1 ml) of the culture was added to 10 ml of LB medium including 50 μg/ml ampicillin and the medium was cultured at 37° C. for 2 hours. Isopropyl β-D thio galactoside (IPTG), which is a transcriptional inducer of lac promoter in the vector, was added to the culture at a final concentration of 1 mM and the culture was incubated at 37° C. for 6 hours. Cells were collected from 1 ml of the culture by centrifugation. To confirm the expression of the protein of the present invention, a western blotting was performed. As a result, the protein expressed in the cells was detected. In contrast, when IPTG was not added to a culture or when the cells not including the expression vector pSHGFAP was cultured, the protein was not expressed.

EXAMPLE 7

Establishment of an Animal Cell Strain Expressing the Protein Having the Protease Activity of the Present Invention Plasmid pNHGFAP, which was prepared in Example 5 and includes the cDNA encoding the protein of the present invention at a restriction enzyme cleavage site of the expression vector pcDNAI/Neo, was recovered from E. coli transformants and purified according to the method of Maniatis et al. ("Molecular Cloning", Cold Spring Harbor Laboratory, 86–96 (1982)) to obtain an expression vector for the protein of the present invention in a large amount.

CHO cells were transformed with the expression vector so obtained according to the method of Ausubel et al. (Current Protocols in Molecular Biology, Green Publishing Associates and Wiley-Inter Science, 9.1.1–9.1.4 (1987)). In more detail, first, CHO cells were cultured in tissue culture dish with a diameter of 9 cm containing ERDF medium (Kyokuto pharmaceutical) supplemented by 10% fetal bovine serum (FBS) until cells were grown to semiconfluence. The medium was then removed from the dish and a DNA solution, which was prepared as described below, was dropwisely added. The DNA solution, for a single dish with a diameter of 9 cm, was prepared by the steps of making 570 μl mixture in an eppendorf tube including 300 μl of 2×HEBS solution (1.6% NaCl, 0,074% KCl, 0.05% disodium hydrogenphosphate 12H$_2$O, 0.2% dextrose, and 1% HEPES, pH7.05), 10 µg plasmid DNA, and sterilized water; dropwisely adding 30 µl of 2.5M CaCl$_2$ solution to the mixture while the mixture was vigorously voltexed for a few second; and allowing the mixture to stand for 30 minutes at room temperature.

The DNA solution thus obtained was applied to the CHO cells and the cells were allowed to stand for 30 minutes at room temperature. Then 9 ml of ERDF medium containing 10% FBS was added to the dish and the cells were cultured for 4 to 5 hours at 37° C. in the presence of 5% CO$_2$. The medium was then removed from the dish. The cells were washed with 5 ml of 1×TBS++solution (25 mM Tris-HCl buffer, pH 7.5, 140 mM NaCl, 5 mM KCl, 0.6 mM disodium hydrogenphosphate, 0.08 mM CaCl$_2$, and 0.08 mM MgCl$_2$). The 1×TBS++solution was then removed. Then, 5 ml of 1×TBS++solution including 20% glycerol was added to the cells and the cells were allowed to stand for 1 to 2 minutes at room temperature and a supernatant was removed. The cells were washed again with 5 ml of 1× TBS++solution. 10 ml of ERDF medium including 10% FBS was added to the dish and then the cells were cultured at 37° C. in the presence of 5% CO$_2$. After 48 hours culture, the medium was removed and the cells were washed with 5 ml of 1×TBS++solution. The cells were then removed from the dish by a trypsin treatment and the cells from one dish were distributed to ten dishes. Agent G418 (G418 sulfate (GENETICIN, GIBCO)) was added to each dish at a concentration of 200 µg/ml and the cells were cultured. After 10 days, vital cells, which resisted G418, were isolated. The cells were then cultured for 7 days in a 24 well plate including 1 ml of ERDF medium supplemented by 10% FBS. Then the cells were cultured in serum-free ERDF medium for 72 hours and the resulting culture in each well was recovered. The culture was concentrated by ultrafiltration and electrophoresed by SDS acrylamide gel electrophoresis. The expression of the protein of the present invention was detected by western blotting.

EXAMPLE 8

Purification and Amino Acid Sequence Analysis of the Precursor Protein With a Molecular Weight of About 96,000 Dalton Blood from a normal individual (human) were mixed with 10 mM EDTA), 10 mM benzamidine (Aldrich Chemical), 5 mM 6-amino-n-caproic acid n-hexyl ester p-toluenesulfate (Tokyo Chemical), 2 mg/ml soybean trypsin inhibitor (Sigma), 50 mM naphamostat mesilate (Torii Pharmaceutical), and 500 KIU/ml aprotinin (Pentapharm). Cells were immediately removed by centrifugation to obtain plasma. After the plasma is diluted with water to three volumes, the diluted plasma was applied on a Heparin-sepharose column (Pharmacia), which had been pre-equilibrated with buffer A (including 10 mM NaH$_2$PO$_4$—Na$_2$HPO$_4$ buffer, pH7, 50 mM NaCl), and the column was washed with buffer A. The column was then eluted with a linear gradient of 50 mM to 700 mM NaCl in Buffer A and buffer B (including 10 mM NaH$_2$PO$_4$—Na$_2$HPO$_4$ buffer, pH7, 700 mM NaCl).

As described in Example 10 infra, fractions including the protein of the present invention (fractions eluted with about 100 mM–250 mM NaCl) were recovered by a sandwich enzyme-linked immunosorbent assay (ELISA) with the use of an antibody that was prepared by immunizing a mouse with the protein derived from human disclosed in Japanese Patent Publication (Kokai) No: 5-103670, fusing single spleen cell from the mouse and a myeloma cell by a standard method to obtain a hybridoma, and obtaining the antibody from the hybridoma. The fractions were mixed with equivalent 2M ammonium sulfate. The mixture was applied to a phenyl-sepharose column (Pharmacia) pre-equilibrated with 1M ammonium sulfate. The column was washed with 1M ammonium sulfate. The column was then eluted with a linear gradient of 1M to 0M ammonium sulfate. Fractions including the protein of the present invention (fractions eluted with about 400 mM–100 mM ammonium sulfate) were recovered by ELISA. The fractions were concentrated with the use of an amicon ultrafiltration membrane YM-30 and buffer C (including 10 mM Tris/HCl buffer, pH 8, 150 mM NaCl) was added. The solution was applied to the antibody affinity column described in Example 3 equilibrated with buffer C. The column was washed with buffer C and eluted with buffer D (50 mM Glycine/HCl buffer, pH3). Fractions were collected and neutralized with buffer E (1M Tris/HCl, pH8). The resulting protein product was activated with thrombin, analyzed to determine amino acid sequence, and electrophoresed by SDS polyacrylamide gel electrophoresis as described below.

To activate the purified protein, it was incubated with 1 unit/ml thrombin (Enzyme Research) in buffer C for 2 hours at 37° C. The resulting activated protein was reduced with 2-mercaptoethanol in buffer F (6M guanidine hydrochloride, 0.002M EDTA, 1M Tris-HCl buffer, pH 8.5) for 2 hours at 40° C. Monoiodoacetic acid at the same concentration as the protein was added to the solution, and the mixture was allowed to react in the presence of nitrogen gas for 1 hour at room temperature in the darkness to carboxymethylate the protein. After the reaction, the resulting solution was applied to YMC pack C4 column (YMC). The column was then eluted with a linear gradient of 10% to 70% acetonytryl/ isopropylalchol (3/7) for 20 minutes and two major peaks were obtained. These peaks were dried under a reduced pressure, dissolved in 60 µl of 50% trifluoroacetic acid (TFA). The solution was added to a glass filter treated with polybrene, and the amino acid sequence of the N terminal of the protein was determined by 470A Sequencer (Applied Biosystems) employing Edman degradation. The identification of each phenylthiohydantoin (PTH) amino acid was performed with the use of MCI gel ODS IHU (0.46× 15 cm) column (Mitsubishi Kasei Crop.). The column was eluted with acetate buffer (10 mM acetate buffer, pH4.7, 0.01% SDS, and 38% acetonitrile) at a flow rate of 1.2 ml/min, at 43° C., and a PTH-amino acid was detected through 269 nm absorbance.

The sequence analysis of the reduced carboxymethylated proteins showed that the N terminal amino acid sequence of one of these polypeptides has the sequence of SEQ ID NO: 11. The N terminal of another peptide was blocked.

EXAMPLE 9

Purification and Amino Acid Sequence Analysis of a Protein With a Molecular Weight of About 34,000 Dalton Blood from a normal individual (human) was mixed with 10 mM EDTA), 10 mM benzamidine (Aldrich Chemical) and 5 mM 6-amino-n-caproic acid n-hexyl ester p-toluensulfonate (Tokyo Chemical). Cells were immediately removed by centrifugation to obtain plasma. The plasma was applied on a Heparin-sepharose column (pharmacia), which had been pre-equilibrated with buffer G (including 10 mM NaH$_2$PO$_4$—Na$_2$HPO$_4$ buffer, pH7, 150 mM NaCl), and the column was washed with buffer G. The column was then eluted with a linear gradient of 150 mM to 700 mM NaCl in buffer G and buffer B (including 10 mM NaH$_2$PO$_4$—Na$_2$HPO$_4$ buffer, pH7, 700 mM NaCl).

As described in Example 10 infra, fractions including the protein of the present invention (fractions eluted with about 300 mM–450 mM NaCl) were recovered by a sandwich enzyme-linked immunosorbent assay (ELISA) by the use of an antibody that was prepared by immunizing a mouse with a human protein disclosed in Japanese Patent Publication (Kokai) No: 5-103670, fusing a single spleen cell from the mouse and a myeloma cell by a standard method to obtain a hybridoma, and obtaining the antibody from the hybridoma. The fractions were applied to a phenyl-sepharose column (Pharmacia) and the column was then eluted with a linear gradient of 1M to 0M ammonium sulfate as described in Example 1. Fractions including the protein of the present invention (fractions eluted with about 700 mM–500 mM ammonium sulfate) was recovered by ELISA. The fractions were concentrated with the use of an amicon ultrafiltration membrane YM-30 and buffer C (including 10 mM Tris/HCl buffer, pH 8, 150 mM NaCl) was added. The solution was applied to an aprotinin immobilized affinity column (Pentapharm) equilibrated with buffer C. The unbound fraction was applied to an antibody affinity column described in Example 3 equilibrated with buffer C. The column was washed with buffer C.

The column was eluted with buffer D (50 mM Glycine/HCl buffer, pH3). Fractions were collected and neutralized with buffer E (1M Tris/HCl, pH8). The resulting protein product was activated with thrombin, analyzed to determine amino acid sequence, and electrophoresed by SDS polyacrylamide gel electrophoresis as described below.

To activate the purified protein, it was incubated with 1 unit/ml thrombin (Enzyme Research) in buffer C for 2 hours at 37° C. The resulting activated protein was reduced with 2-mercaptoethanol in buffer F (6M guanidine hydrochloride, 0,002M EDTA, 1M Tris-HCl buffer, pH 8.5) for 2 hours at 40° C. Monoiodoacetic acid at the same concentration as the protein was added to the solution, and the mixture was allowed to react in the presence of nitrogen gas for 1 hour at room temperature in the darkness to carboxymethylate the protein. After the reaction, the resulting solution was applied to YMC pack C4 column (YMC). The column was then eluted with a linear gradient of 10% to 70% acetonytryl/isopropylalchol (3/7) for 30 minutes and the peaks were obtained. These peaks were dried under a reduced pressure, dissolved in 60 µl of 50% trifluoroacetic acid (TFA). The solution was added to a glass filter treated with polybrene, and the amino acid sequences of the N terminal of the proteins were determined by 470A Sequencer (Applied Biosystems) employing Edman degradation. The identification of each phenylthiohydantoin (PTH) amino acid was performed with the use of MCI gel ODS IHU (0.46×15 cm) column (Mitsubishi Kasei Corp.). The column was eluted with acetate buffer (10 mM acetate buffer, pH4.7, 0.01% SDS, and 38% acetonitrile) at a flow rate of 1.2 ml/min, at 43° C., and a PTH-amino acid was detected through 269 nm absorbance.

The sequence analysis of the reduced carboxymethylated proteins showed that the N terminal amino acid sequence of one of these polypeptides has the sequence of SEQ ID NO: 11.

EXAMPLE 10

Preparation of an Antibody, ELISA Using the Same, and Preparation of an Antibody Affinity Column A Balb/c mouse was immunized with a novel human protein disclosed in Japanese Patent Publication (Kokai) No. 5-103670 by a standard method. The mouse was first immunized with about 10 µg antigen with Freund's complete adjuvant and then boosted with about 10 µg antigen with Freund's incomplete adjuvant intraperitoneally. The mouse was given a final boost from tail vein. Three days after the final boost, spleen cells of the mouse were taken. Single cell of the mouse spleen was fused with mouse myeloma cell P3U1 in the presence of polyethylene glycol by a standard method. Fused cells were screened by the use of enzyme-labeled anti mouse antibodies by ELISA method employing immobilized antigens to select hybridomas producing antibodies against the protein. Each of the obtained hybridomas was cultured in serum-free medium. The supernatant of the culture was applied to a Protein A affinity column to obtain antibodies. Two antibodies recognizing discrete antigenic determinants were used to perform ELISA by a standard method. The second antibody was labeled with peroxidase by a standard method. One of the obtained antibodies was used to couple to CNBr-sepharose (Pharmacia) to obtain an antibody affinity column.

EXAMPLE 11

SDS Polyacrylamide Gel Electrophoresis

To determine apparent molecular weights of the proteins purified as described in Examples 8 and 9, SDS polyacrylamide gel electrophoresis was conducted. The perified proteins were electrophoresed by SDS polyacrylamide gel electrophoresis involving 12.5% polyacrylamide slab gel under a non reduced condition. Molecular makers were available from Pharmacia. After electrophoresis, the gel was stained with Coomassie Brilliant Blue (CBB) R250. The protein prepared in Example 8 was 96,000 dalton and the protein prepared in Example 9 was 34,000 dalton determined by SDS polyacrylamide gel electrophoresis. The sizes of these proteins were estimated by comparing the location of the bands of the proteins to the location of the bands of the marker.

EXAMPLE 12

Activation and Assay

To activate the proteins purified in Examples 8 and 9, these proteins were incubated with 1 unit/ml thrombin (Enzyme Research) in buffer C for 2 hours at 37° C. Each of the activated proteins was added to 40 µl of the solution described in the reference example in Japanese Patent Application No. 3-271362. This solution included 10 mM benzamidine, 100 mM NaCl, 50 mM Tris-HCl buffer, pH 8, and 5 µg of single-chain human HGF. After 2 hours incubation at 37° C., SDS polyacrylamide gel electrophoresis was done on the mixture under a reduced condition. After electrophoresis, the gel was stained with CBB. The activity of the protein was determined by the ratio of single-chain HGF to two-chain HGF. The result was shown in FIG. 2, wherein 1 represents the result in the presence of about 100 ng/ml protein obtained by the activation of the protein having a molecular weight of about 96,000 dalton, 2 represents the result in the presence of about 100 ng/ml protein obtained by the activation of the protein having a molecular weight of about 34,000 dalton, and 3 represents the result in the absence of the proteins.

EXAMPLE 13

Purification of the Precursor Proteins and Analysis of the N-Terminal Amino Acid Sequences of the Proteins The protein, which has a molecular weight of about 96,000 dalton determined by SDS polyacrylamide gel electrophoresis and acquired a protease activity to convert single-chain HGF into two-chain HGF by the treatment with a serine protease, was obtained from human plasma according to the method described in Example 8. This purified protein was reduced with 2-mercaptoethanol in buffer A (6M guanidine hydrochloride, 0.002M EDTA, and 1M Tris-HCl buffer, pH 8.5) for 2 hours at 40° C. Monoiodoacetic acid at the same concentration as the protein was added to the solution, and the mixture was allowed to react in the presence of nitrogen gas for 1 hour at a room temperature in the darkness to carboxymethylate the protein. After the reaction, the resulting solution was applied to YMC pack C4 column (YMC). The column was then eluted with a linear gradient of 10% to 70% acetonytryl/isopropylalchol (3/7) for 30 minutes and a single major peak was detected.

The fraction corresponding to the peak was dissolved in 0.1% ammonium bicarbonate including 2M urea. TPCK-trypsin (Miles Laboratory) or TLCK-chymotrypsin (Miles Laboratory) was added to the solution in a ratio of enzyme:substrate=1:50 and the mixture was allowed to react for 16 hours at 37° C. The reaction mixture was applied to HPLC and the column was eluted with a linear gradient of 0% to 80% acetonitrile/isopropyl alcohol (3/7) for 1 hour to obtain multiple peptide fragments.

These peptide fragments were dried in the air and dissolved in 60 µl of 50% trifluoroacetic acid (TFA). The solution was added to a glass filter treated with polybrene, and the amino acid sequence of the protein was determined by $470A Sequencer (Applied Biosystems) involving Edman degradation. The identification of phenylthiohydantoin (PTH) amino acid was performed with the use of MCI gel ODS IHU (0.46×15 cm) column (Mitsubishi Kasei Corp.). The column was eluted with acetate buffer (10 mM acetate buffer, pH4.7, 0.01% SDS, and 38% acetonitrile) at a flow rate of 12 ml/min, at 43° C. and a PTH-amino acid was detected through 269 nm absorbance. The amino acid sequences of two of these peptides are shown in SEQ ID NO:6 and 7.

EXAMPLE 14

Preparation of DNA Fragment Including Parts of the Gene Encoding the Precursor Protein by PCR Commercially available human liver cDNA bank (Quick-clone™ human liver cDNA, Clonetech) was used as a template DNA. PCR was performed by Perkin Elmer Cetus DNA Thermal Cycler with the use of Gene Amp DNA Amplification Reagent Kit (Takara Shuzo Co. Ltd.). First, 100 µl of reaction mixture was prepared including a template DNA (1 ng), 10 µl of x10 reaction buffer (500 mM KCl, 100 mM Tris-HCl buffer, pH8.3, 15 mM $MgCl_2$, and 0.1% (w/v) gelatin), 2 µl each of 10 mM dGTP, dATP, dCTP, and dTTP, 2 µl of (+) strand DNA primer of SEQ ID NO: 4 as primer #1, 0.1 µM (–) strand DNA primer of SEQ ID NO: 5 as primer #2 to make final concentration to 0.1 µM, 0.5 µl of Taq DNA polymerase, and sterilized deionized water. Template DNA was then amplified by 30 cycles of the PCR including pretreatment at 94° C. for 10 minutes, denaturation at 94° C. for 1 minute, annealing at 37° C. for 2 minutes, and extention at 72° C. for 3 minutes. The reaction was stopped by incubation at 72° C. for 7 minutes. The resulting reaction mixture was extracted with phenol:chloroform=1:1, and the resulting DNAs were ethanol precipitated. The precipitate was dissolved in 21.5 µl of sterilized deionized water. Then, 2.5 µl of x10 restriction enzyme buffer (50 mM Tris-HCl buffer, pH7.5, 10 mM $MgCl_2$, 100 mM KCl, and 1 mM DTT) and 1 µl of restriction enzyme BglII (15 units) were added to the solution and the resulting mixture was allowed to react at 37° C. for 2 hours. The reaction mixture was electrophoresed using 5% polyacrylamide gel, the 323 bp band was extracted from the gel by a standard technique to recover a DNA fragment, and ethanol precipitated.

The DNA fragment was inserted into pUC19 vector at BamHI site and the base sequence thereof was identified according to a standard method. The base sequence of the identified DNA fragment prepared by PCR is shown in SEQ ID NO: 13.

EXAMPLE 15

Screening for a DNA Fragment Including Complete Gene Encoding the Precursor Protein of the Present Invention The 323 bp fragment prepared as described in Example 14 was labeled with $^{32}P$ according to the method described in "Molecular Cloning" (Cold Spring Harbor Laboratory, 1982) and used as a probe for screening. The library to be screened was Premade Lambda Phage Library (Stratagene), which was a human liver cDNA library derived from 49 years old male. E. coli XL1-Blue (Stratagene) was infected with the phage to make about 500 million plaques. The infected cells were cultured on NZY medium and then transferred on Gene Screen Plus membranes (Dupont). The membranes were allowed to stand on paper filters soaked with 0.1M NaOH—0.5M NaCl for 2 minutes, and then on paper filters soaked with 1.5M NaCl—0.5M Tris—HCl buffer (pH7.5) for 5 minutes. The membranes were further treated two more times, washed with 2×SSC, and dried on a dried paper filter in the air. DNAs on the membranes were fixed with UV light at 120 mJ/cm².

Five membranes thus treated were soaked in 50 ml of solution including 50 mM Tris-HCl buffer, pH 7.5, 1M NaCl, and 1% SDS and allowed to stand at 65° C. for 2 hours. The membranes were hybridized in 40 ml of solution including 5 ng/ml P labeled probe, 100 µg/ml salmon sperm DNA, 50 mM Tris-HCl buffer, pH 7.5, 1M NaCl, and 1% SDS at 65° C. for 16 hours. The membranes were then washed in 2×SSC at a room temperature for 5 minutes, 0.1×SSC at a room temperature for 30 minutes for two times, and autoradiographed by a standard method, thereby positive clones were obtained.

EXAMPLES 16

Subcloning of DNA Fragments and Identification of the Base Sequences Thereof Plasmids were prepared directly from positive phage clones obtained in Example 15 by the excision method. Phage was extracted from single plaque by the treatment with 500 µl of SM buffer (50 mM Tris-HCl buffer, pH 7.5, 100 mM NaCl, 10 mM $Mg_2SO_4$, and 0.01% gelatin) and 20 µl of chloroform. A mixture including 200 µl of the above-mentioned phage extract, 200 μl of XL1-Blue, and 1 μl of R408 helper phage was allowed to stand 37° C. for 15 minutes. Then 5 ml of 2×YT medium was added to the mixture and the resulting solution was shake cultured at 37° C. for 3 hours. The culture was then heated to 70° C. for 20 minutes followed by centrifugation at 4000 g for 5 minutes to obtain a supernatant. The supernatant was diluted to make 100-fold diluted solution. Then 20 μl of the diluted solution was mixed with 200 μl of XL1-Blue and the mixture was allowed to react at 37° C. for 15 minutes. Then 2 μl of the resulting mixture was plated onto a LB agarose medium including 40 μl/ml ampicillin. Twenty-four plasmids from the colonies which appeared on the plate were obtained and analyzed. The base sequence thus determined is shown in SEQ ID NO: 3. Based on this base sequence, the amino acid sequence of the precursor protein of the present invention was deduced (SEQ ID NO: 12).

The present invention enables a stable and simple production of a protein having the protease activity which converts single-chain HGF to active two-chain HGF and the precursor protein thereof in a large amount. These proteins can be used as a regulator in producing active HGF.

What is claimed is:

1. A DNA fragment comprising a gene encoding a protein having the amino acid sequence of SEQ ID NO: 1.

2. The DNA fragment according to claim 1, wherein said gene comprises the base sequence of SEQ ID NO: 2.

3. The DNA fragment according to claim 1, wherein said gene has the base sequence of SEQ ID NO: 3.

4. An expression vector comprising the DNA fragment according to claim 1, wherein said gene is positioned downstream of a promoter so as to express a polypeptide encoded by the gene.

5. A transformant obtained by transformation of a host cell with the vector according to claim 4.

6. A method for producing a protein having the amino acid sequence of SEQ ID NO: 1, comprising the steps of culturing the transformant according to claim 5, wherein said DNA fragment is ligated at its 5' terminal end to said expression vector by a linker having the nucleotide sequence of SEQ ID NO: 10 to produce a protein having the amino acid sequence of SEQ ID NO: 1 and having at its N-terminal end the amino acid sequence of apolipoprotein E encoded by the linker, and cleaving the N-terminal end amino acid sequence of apolipoprotein E to yield the protein having the sequence according to SEQ ID NO: 1.

7. A DNA fragment comprising a gene encoding a protein having the amino acid sequence of SEQ ID NO: 12.

8. The DNA fragment according to claim 7, wherein said gene comprises the base sequence of SEQ ID NO: 13.

9. The DNA fragment according to claim 7, wherein said gene has the base sequence of SEQ ID NO: 14.

10. An expression vector comprising the DNA fragment according to claim 7, wherein said gene is positioned downstream of a promoter so as to express a polypeptide encoded by the gene.

11. A transformant obtained by transformation of a host cell with the vector according to claim 10.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 300 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: human ( x i ) SEQUENCE DESCRIPTION: SEQ ID NO:1:

```
Ala  Leu  Ser  Trp  Glu  Tyr  Cys  Arg  Leu  Glu  Ala  Cys  Glu  Ser  Leu  Thr
 1              5                          10                         15

Arg  Val  Gln  Leu  Ser  Pro  Asp  Leu  Leu  Ala  Thr  Leu  Pro  Glu  Pro  Ala
               20                         25                         30

Ser  Pro  Gly  Arg  Gln  Ala  Cys  Gly  Arg  Arg  His  Lys  Lys  Arg  Thr  Phe
               35                         40                    45

Leu  Arg  Pro  Arg  Ile  Ile  Gly  Gly  Ser  Ser  Ser  Leu  Pro  Gly  Ser  His
      50                         55                        60

Pro  Trp  Leu  Ala  Ala  Ile  Tyr  Ile  Gly  Asp  Ser  Phe  Cys  Ala  Gly  Ser
 65                            70                    75                      80

Leu  Val  His  Thr  Cys  Trp  Val  Val  Ser  Ala  Ala  His  Cys  Phe  Ser  His
                    85                         90                       95

Ser  Pro  Pro  Arg  Asp  Ser  Val  Ser  Val  Val  Leu  Gly  Gln  His  Phe  Phe
```

|  |  |  |  |  |  |  | 100 |  |  |  |  | 105 |  |  |  |  | 110 |  |  |
|---|---|---|---|---|---|---|---|---|---|---|---|---|---|---|---|---|---|---|---|

Asn Arg Thr Thr Asp Val Thr Gln Thr Phe Gly Ile Glu Lys Tyr Ile
          115                   120              125

Pro Tyr Thr Leu Tyr Ser Val Phe Asn Pro Ser Asp His Asp Leu Val
    130                 135              140

Leu Ile Arg Leu Lys Lys Lys Gly Asp Arg Cys Ala Thr Arg Ser Gln
145              150             155              160

Phe Val Gln Pro Ile Cys Leu Pro Glu Pro Gly Ser Thr Phe Pro Ala
             165            170              175

Gly His Lys Cys Gln Ile Ala Gly Trp Gly His Leu Asp Glu Asn Val
         180              185            190

Ser Gly Tyr Ser Ser Ser Leu Arg Glu Ala Leu Val Pro Leu Val Ala
      195             200            205

Asp His Lys Cys Ser Ser Pro Glu Val Tyr Gly Ala Asp Ile Ser Pro
   210               215              220

Asn Met Leu Cys Ala Gly Tyr Phe Asp Cys Lys Ser Asp Ala Cys Gln
225              230           235              240

Gly Asp Ser Gly Gly Pro Leu Ala Cys Glu Lys Asn Gly Val Ala Tyr
             245            250              255

Leu Tyr Gly Ile Ile Ser Trp Gly Asp Gly Cys Gly Arg Leu His Lys
         260              265            270

Pro Gly Val Tyr Thr Arg Val Ala Asn Tyr Val Asp Trp Ile Asn Asp
      275             280            285

Arg Ile Arg Pro Pro Arg Arg Leu Val Ala Pro Ser
   290               295           300

( 2 ) INFORMATION FOR SEQ ID NO:2:

( i ) SEQUENCE CHARACTERISTICS:
        ( A ) LENGTH: 329 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: human ( v i i ) IMMEDIATE SOURCE:
        ( A ) LIBRARY: Quick-cloneTM human liver cDNA (Clonetech)

( x i ) SEQUENCE DESCRIPTION: SEQ ID NO:2:

GGATCC CAG ATT GCG GGC TGG GGC CAC TTG GAT GAG AAC GTG AGC GGC    48
       Gln Ile Ala Gly Trp Gly His Leu Asp Glu Asn Val Ser Gly
        1             5                   10

TAC TCC AGC TCC CTG CGG GAG GCC CTG GTC CCC CTG GTC GCC GAC CAC    96
Tyr Ser Ser Ser Leu Arg Glu Ala Leu Val Pro Leu Val Ala Asp His
15                20              25              30

AAG TGC AGC AGC CCT GAG GTC TAC GGC GCC GAC ATC AGC CCC AAC ATG    144
Lys Cys Ser Ser Pro Glu Val Tyr Gly Ala Asp Ile Ser Pro Asn Met
              35              40              45

CTC TGT GCC GGC TAC TTC GAC TGC AAG TCC GAC GCC TGC CAG GGG GAC    192
Leu Cys Ala Gly Tyr Phe Asp Cys Lys Ser Asp Ala Cys Gln Gly Asp
          50                55              60

TCA GGG GGG CCC CTG GCC TGC GAG AAG AAC GGC GTG GCT TAC CTC TAC    240
Ser Gly Gly Pro Leu Ala Cys Glu Lys Asn Gly Val Ala Tyr Leu Tyr
    65                  70              75

GGC ATC ATC AGC TGG GGT GAC GGC TGC GGG CGG CTC CAC AAG CCG GGG    288
Gly Ile Ile Ser Trp Gly Asp Gly Cys Gly Arg Leu His Lys Pro Gly

|   |   |   | 80 |   |   |   | 85 |   |   |   | 90 |   |   |   |
|---|---|---|---|---|---|---|---|---|---|---|---|---|---|---|
| GTC | TAC | ACC | CGC | GTG | GCC | AAC | TAT | GTG | GAC | TGG | AT GGATCC | | | 329 |
| Val | Tyr | Thr | Arg | Val | Ala | Asn | Tyr | Val | Asp | Trp | | | | |
| 95 | | | | | 100 | | | | | 105 | | | | |

(2) INFORMATION FOR SEQ ID NO:3:

(i) SEQUENCE CHARACTERISTICS:
        (A) LENGTH: 970 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human (vii) IMMEDIATE SOURCE:
        (A) LIBRARY: Pre-made Lambda phage Library, human liver (49, male) cDNA Library (Stratagene)

(xi) SEQUENCE DESCRIPTION: SEQ ID NO:3:

| GCGCGCTCTC | CTGGGAGTAC | TGCCGCCTGG | AGGCCTGCGA | ATCCCTCACC | AGAGTCCAAC | 60 |
|---|---|---|---|---|---|---|
| TGTCACCGGA | TCTCCTGGCG | ACCCTGCCTG | AGCCAGCCTC | CCCGGGGCGC | CAGGCCTGCG | 120 |
| GCAGGAGGCA | CAAGAAGAGG | ACGTTCCTGC | GGCCACGTAT | CATCGGCGGC | TCCTCCTCGC | 180 |
| TGCCCGGCTC | GCACCCCTGG | CTGGCCGCCA | TCTACATCGG | GGACAGCTTC | TGCGCCGGGA | 240 |
| GCCTGGTCCA | CACCTGCTGG | GTGGTGTCGG | CCGCCCACTG | CTTCTCCCAC | AGCCCCCCA | 300 |
| GGGACAGCGT | CTCCGTGGTG | CTGGGCCAGC | ACTTCTTCAA | CCGCACGACG | GACGTGACGC | 360 |
| AGACCTTCGG | CATCGAGAAG | TACATCCCGT | ACACCCTGTA | CTCGGTGTTC | AACCCCAGCG | 420 |
| ACCACGACCT | CGTCCTGATC | CGGCTGAAGA | AGAAAGGGGA | CCGCTGTGCC | ACACGCTCGC | 480 |
| AGTTCGTGCA | GCCCATCTGC | CTGCCCGAGC | CCGGCAGCAC | CTTCCCCGCA | GGACACAAGT | 540 |
| GCCAGATTGC | GGGCTGGGGC | CACTTGGATG | AGAACGTGAG | CGGCTACTCC | AGCTCCCTGC | 600 |
| GGGAGGCCCT | GGTCCCCCTG | GTCGCCGACC | ACAAGTGCAG | CAGCCCTGAG | GTCTACGGCG | 660 |
| CCGACATCAG | CCCCAACATG | CTCTGTGCCG | GCTACTTCGA | CTGCAAGTCC | GACGCCTGCC | 720 |
| AGGGGACTC | AGGGGGGCCC | CTGGCCTGCG | AGAAGAACGG | CGTGGCTTAC | CTCTACGGCA | 780 |
| TCATCAGCTG | GGGTGACGGC | TGCGGGCGGC | TCCACAAGCC | GGGGGTCTAC | ACCCGCGTGG | 840 |
| CCAACTATGT | GGACTGGATC | AACGACCGGA | TACGGCCTCC | CAGGCGGCTT | GTGGCTCCCT | 900 |
| CCTGACCCTC | CAGCGGGACA | CCCTGGTTCC | CACCATTCCC | TGCCTTGCTG | ACAATAAAGA | 960 |
| TATTTCCAAG | | | | | | 970 |

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: Other nucleic acid (synthetic DNA)

(vi) ORIGINAL SOURCE:
        (A) ORGANISM: human (xi) SEQUENCE DESCRIPTION: SEQ ID NO:4:

| CTCGGATCCC | ARATNGCNGG | NTGGGG | 26 |
|---|---|---|---|

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( v i ) ORIGINAL SOURCE:
        ( A ) ORGANISM: human ( x i ) SEQUENCE DESCRIPTION: SEQ ID NO:5:

CTCGGATCCA TCCARTCNAC RTARTT　　　　　　　　　　　　　　　　　　26

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: human ( x i ) SEQUENCE DESCRIPTION: SEQ ID NO:6:

Cys Gln Ile Ala Gly Trp Gly
 1　　　　　　　　　5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: human ( x i ) SEQUENCE DESCRIPTION: SEQ ID NO:7:

Val Ala Asn Tyr Val Asp Trp Ile
 1　　　　　　　　　5

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( v i ) ORIGINAL SOURCE:
        ( A ) ORGANISM: human ( x i ) SEQUENCE DESCRIPTION: SEQ ID NO:8:

GTCCAACTGT CACCGGATC　　　　　　　　　　　　　　　　　　　　　19

( 2 ) INFORMATION FOR SEQ ID NO:9:

( i ) SEQUENCE CHARACTERISTICS:
        ( A ) LENGTH: 19 base pairs
        ( B ) TYPE: nucleic acid (C) STRANDEDNESS: double
(D) TOPOLOGY: linear (ii) MOLECULE TYPE: Other nucleic acid (synthetic DNA)

(vi) ORIGINAL SOURCE:
(A) ORGANISM: human (xi) SEQUENCE DESCRIPTION: SEQ ID NO:9:

CGCTCGAGGG TCAGGAGGG    19

(2) INFORMATION FOR SEQ ID NO:10:

(i) SEQUENCE CHARACTERISTICS:
(A) LENGTH: 71 base pairs
(B) TYPE: nucleic acid
(C) STRANDEDNESS: double
(D) TOPOLOGY: linear (ii) MOLECULE TYPE: Other nucleic acid (synthetic DNA)

(vi) ORIGINAL SOURCE:
(A) ORGANISM: human (xi) SEQUENCE DESCRIPTION: SEQ ID NO:10:

AATTCGGATC CATGAAGGTT CTGTGGGCTG CGTTGCTGGT CACATTCCTG GCAGGATGCC    60
     GCCTAG GTACTTCCAA GACACCCGAC GCAACGACCA GTGTAAGGAC CGTCCTACGG

AGGCCAAGGT G    71
TCCGGTTCCA C (2) INFORMATION FOR SEQ ID NO:11:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: human (xi) SEQUENCE DESCRIPTION: SEQ ID NO:11:

Ile Ile Gly Gly Ser Ser Ser Leu
 1               5

(2) INFORMATION FOR SEQ ID NO:12:

(i) SEQUENCE CHARACTERISTICS:
(A) LENGTH: 655 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: human (xi) SEQUENCE DESCRIPTION: SEQ ID NO:12:

Met Gly Arg Trp Ala Trp Val Pro Ser Pro Trp Pro Pro Pro Gly Leu
 1               5                  10                  15

Gly Pro Phe Leu Leu Leu Leu Leu Leu Leu Leu Leu Pro Arg Gly
                20                  25                  30

Phe Gln Pro Gln Pro Gly Gly Asn Arg Thr Glu Ser Pro Glu Pro Asn
            35                  40                  45

Ala Thr Ala Thr Pro Ala Ile Pro Thr Ile Leu Val Thr Ser Val Thr

-continued

|     |     |     | 50  |     |     |     | 55  |     |     |     | 60  |     |     |     |
| --- | --- | --- | --- | --- | --- | --- | --- | --- | --- | --- | --- | --- | --- | --- |
| Ser | Glu | Thr | Pro | Ala | Thr | Ser | Ala | Pro | Glu | Ala | Glu | Gly | Pro | Gln | Ser |
| 65  |     |     |     |     | 70  |     |     |     |     | 75  |     |     |     |     | 80  |
| Gly | Gly | Leu | Pro | Pro | Pro | Arg | Ala | Val | Pro | Ser | Ser | Ser | Ser | Pro |
|     |     |     |     | 85  |     |     |     |     | 90  |     |     |     |     | 95  |
| Gln | Ala | Gln | Ala | Leu | Thr | Glu | Asp | Gly | Arg | Pro | Cys | Arg | Phe | Pro | Phe |
|     |     |     | 100 |     |     |     |     | 105 |     |     |     |     | 110 |     |     |
| Arg | Tyr | Gly | Gly | Arg | Met | Leu | His | Ala | Cys | Thr | Ser | Glu | Gly | Ser | Ala |
|     |     |     | 115 |     |     |     |     | 120 |     |     |     |     | 125 |     |     |
| His | Arg | Lys | Trp | Cys | Ala | Thr | His | Asn | Tyr | Asp | Arg | Asp | Arg | Ala |
|     |     | 130 |     |     |     |     | 135 |     |     |     |     | 140 |     |     |
| Trp | Gly | Tyr | Cys | Val | Glu | Ala | Thr | Pro | Pro | Gly | Gly | Pro | Ala | Ala |
| 145 |     |     |     |     | 150 |     |     |     |     | 155 |     |     |     |     | 160 |
| Leu | Asp | Pro | Cys | Ala | Ser | Gly | Pro | Cys | Leu | Asn | Gly | Gly | Ser | Cys | Ser |
|     |     |     |     | 165 |     |     |     |     | 170 |     |     |     |     | 175 |     |
| Asn | Thr | Gln | Asp | Pro | Gln | Ser | Tyr | His | Cys | Ser | Cys | Pro | Arg | Ala | Phe |
|     |     |     | 180 |     |     |     |     | 185 |     |     |     |     | 190 |     |     |
| Thr | Gly | Lys | Asp | Cys | Gly | Thr | Glu | Lys | Cys | Phe | Asp | Glu | Thr | Arg | Tyr |
|     |     | 195 |     |     |     |     | 200 |     |     |     |     | 205 |     |     |     |
| Glu | Tyr | Leu | Glu | Gly | Gly | Asp | Arg | Trp | Ala | Arg | Val | Arg | Gln | Gly | His |
|     | 210 |     |     |     |     | 215 |     |     |     |     | 220 |     |     |     |     |
| Val | Glu | Gln | Cys | Glu | Cys | Phe | Gly | Gly | Arg | Thr | Trp | Cys | Glu | Gly | Thr |
| 225 |     |     |     |     | 230 |     |     |     |     | 235 |     |     |     |     | 240 |
| Arg | His | Thr | Ala | Cys | Leu | Ser | Ser | Pro | Cys | Leu | Asn | Gly | Gly | Thr | Cys |
|     |     |     |     | 245 |     |     |     |     | 250 |     |     |     |     | 255 |     |
| His | Leu | Ile | Val | Ala | Thr | Gly | Thr | Thr | Val | Cys | Ala | Cys | Pro | Pro | Gly |
|     |     |     | 260 |     |     |     |     | 265 |     |     |     |     | 270 |     |     |
| Phe | Ala | Gly | Arg | Leu | Cys | Asn | Ile | Glu | Pro | Asp | Glu | Arg | Cys | Phe | Leu |
|     |     |     | 275 |     |     |     |     | 280 |     |     |     |     | 285 |     |     |
| Gly | Asn | Gly | Thr | Gly | Tyr | Arg | Gly | Val | Ala | Ser | Thr | Ser | Ala | Ser | Gly |
|     | 290 |     |     |     |     | 295 |     |     |     |     | 300 |     |     |     |     |
| Leu | Ser | Cys | Leu | Ala | Trp | Asn | Ser | Asp | Leu | Leu | Tyr | Gln | Glu | Leu | His |
| 305 |     |     |     |     | 310 |     |     |     |     | 315 |     |     |     |     | 320 |
| Val | Asp | Ser | Val | Gly | Ala | Ala | Ala | Leu | Leu | Gly | Leu | Gly | Pro | His | Ala |
|     |     |     |     | 325 |     |     |     |     | 330 |     |     |     |     | 335 |     |
| Tyr | Cys | Arg | Asn | Pro | Asp | Asn | Asp | Glu | Arg | Pro | Trp | Cys | Tyr | Val | Val |
|     |     |     | 340 |     |     |     |     | 345 |     |     |     |     | 350 |     |     |
| Lys | Asp | Ser | Ala | Leu | Ser | Trp | Glu | Tyr | Cys | Arg | Leu | Glu | Ala | Cys | Glu |
|     |     | 355 |     |     |     |     | 360 |     |     |     |     | 365 |     |     |     |
| Ser | Leu | Thr | Arg | Val | Gln | Leu | Ser | Pro | Asp | Leu | Leu | Ala | Thr | Leu | Pro |
|     | 370 |     |     |     |     | 375 |     |     |     |     | 380 |     |     |     |     |
| Glu | Pro | Ala | Ser | Pro | Gly | Arg | Gln | Ala | Cys | Gly | Arg | Arg | His | Lys | Lys |
| 385 |     |     |     |     | 390 |     |     |     |     | 395 |     |     |     |     | 400 |
| Arg | Thr | Phe | Leu | Arg | Pro | Arg | Ile | Ile | Gly | Gly | Ser | Ser | Ser | Leu | Pro |
|     |     |     |     | 405 |     |     |     |     | 410 |     |     |     |     | 415 |     |
| Gly | Ser | His | Pro | Trp | Leu | Ala | Ala | Ile | Tyr | Ile | Gly | Asp | Ser | Phe | Cys |
|     |     |     | 420 |     |     |     |     | 425 |     |     |     |     | 430 |     |     |
| Ala | Gly | Ser | Leu | Val | His | Thr | Cys | Trp | Val | Val | Ser | Ala | Ala | His | Cys |
|     |     | 435 |     |     |     |     | 440 |     |     |     |     | 445 |     |     |     |
| Phe | Ser | His | Ser | Pro | Pro | Arg | Asp | Ser | Val | Ser | Val | Val | Leu | Gly | Gln |
|     |     | 450 |     |     |     |     | 455 |     |     |     |     | 460 |     |     |     |
| His | Phe | Phe | Asn | Arg | Thr | Thr | Asp | Val | Thr | Gln | Thr | Phe | Gly | Ile | Glu |
| 465 |     |     |     |     | 470 |     |     |     |     | 475 |     |     |     |     | 480 |

```
Lys Tyr Ile Pro Tyr Thr Leu Tyr Ser Val Phe Asn Pro Ser Asp His
            485             490                 495
Asp Leu Val Leu Ile Arg Leu Lys Lys Lys Gly Asp Arg Cys Ala Thr
            500             505                 510
Arg Ser Gln Phe Val Gln Pro Ile Cys Leu Pro Glu Pro Gly Ser Thr
        515             520             525
Phe Pro Ala Gly His Lys Cys Gln Ile Ala Gly Trp Gly His Leu Asp
    530             535             540
Glu Asn Val Ser Gly Tyr Ser Ser Ser Leu Arg Glu Ala Leu Val Pro
545             550             555                 560
Leu Val Ala Asp His Lys Cys Ser Ser Pro Glu Val Tyr Gly Ala Asp
            565             570             575
Ile Ser Pro Asn Met Leu Cys Ala Gly Tyr Phe Asp Cys Lys Ser Asp
            580             585             590
Ala Cys Gln Gly Asp Ser Gly Gly Pro Leu Ala Cys Glu Lys Asn Gly
        595             600             605
Val Ala Tyr Leu Tyr Gly Ile Ile Ser Trp Gly Asp Gly Cys Gly Arg
    610             615             620
Leu His Lys Pro Gly Val Tyr Thr Arg Val Ala Asn Tyr Val Asp Trp
625             630             635                 640
Ile Asn Asp Arg Ile Arg Pro Pro Arg Arg Leu Val Ala Pro Ser
            645             650             655
```

( 2 ) INFORMATION FOR SEQ ID NO:13:

( i ) SEQUENCE CHARACTERISTICS:
        ( A ) LENGTH: 329 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: human ( v i i ) IMMEDIATE SOURCE:
        ( A ) LIBRARY: Quick-cloneTM human liver cDNA (Clonetech)

( x i ) SEQUENCE DESCRIPTION: SEQ ID NO:13:

```
GGATCC CAG ATT GCG GGC TGG GGC CAC TTG GAT GAG AAC GTG AGC GGC       48
       Gln Ile Ala Gly Trp Gly His Leu Asp Glu Asn Val Ser Gly
        1             5                  10

TAC TCC AGC TCC CTG CGG GAG GCC CTG GTC CCC CTG GTC GCC GAC CAC       96
Tyr Ser Ser Ser Leu Arg Glu Ala Leu Val Pro Leu Val Ala Asp His
 15              20              25                  30

AAG TGC AGC AGC CCT GAG GTC TAC GGC GCC GAC ATC AGC CCC AAC ATG      144
Lys Cys Ser Ser Pro Glu Val Tyr Gly Ala Asp Ile Ser Pro Asn Met
                 35              40              45

CTC TGT GCC GGC TAC TTC GAC TGC AAG TCC GAC GCC TGC CAG GGG GAC      192
Leu Cys Ala Gly Tyr Phe Asp Cys Lys Ser Asp Ala Cys Gln Gly Asp
             50              55              60

TCA GGG GGG CCC CTG GCC TGC GAG AAG AAC GGC GTG GCT TAC CTC TAC      240
Ser Gly Gly Pro Leu Ala Cys Glu Lys Asn Gly Val Ala Tyr Leu Tyr
         65              70              75

GGC ATC ATC AGC TGG GGT GAC GGC TGC GGG CGG CTC CAC AAG CCG GGG      288
Gly Ile Ile Ser Trp Gly Asp Gly Cys Gly Arg Leu His Lys Pro Gly
     80              85              90

GTC TAC ACC CGC GTG GCC AAC TAT GTG GAC TGG AT GGATCC                329
Val Tyr Thr Arg Val Ala Asn Tyr Val Asp Trp
```

(2) INFORMATION FOR SEQ ID NO:14:

(i) SEQUENCE CHARACTERISTICS:
    (A) LENGTH: 2033 base pairs
    (B) TYPE: nucleic acid
    (C) STRANDEDNESS: double
    (D) TOPOLOGY: linear (ii) MOLECULE TYPE: cDNA (vi) ORIGINAL SOURCE:
    (A) ORGANISM: human (vii) IMMEDIATE SOURCE:
    (A) LIBRARY: Pre-made Lambda phage Library,
      human liver(49, male) cDNA Library (Stratagene)

(xi) SEQUENCE DESCRIPTION: SEQ ID NO:14:

```
ATGGGGCGCT GGGCCTGGGT CCCCAGCCCC TGGCCCCCAC CGGGGCTGGG CCCCTTCCTC    60
CTCCTCCTCC TGCTGCTGCT GCTGCTGCCA CGGGGGTTCC AGCCCCAGCC TGGCGGGAAC   120
CGTACGGAGT CCCCAGAACC TAATGCCACA GCGACCCCTG CGATCCCCAC TATCCTGGTG   180
ACCTCTGTGA CCTCTGAGAC CCCAGCAACA AGTGCTCCAG AGGCAGAGGG ACCCCAAAGT   240
GGGGGGCTCC CGCCCCCGCC CAGGGCAGTT CCCTCGAGCA GTAGCCCCCA GGCCCAAGCA   300
CTCACCGAGG ACGGGAGGCC CTGCAGGTTC CCCTTCCGCT ACGGGGCCG  CATGCTGCAT   360
GCCTGCACTT CGGAGGGCAG TGCACACAGG AAGTGGTGTG CCACAACTCA CAACTACGAC   420
CGGGACAGGG CCTGGGGCTA CTGTGTGGAG GCCACCCCGC CTCCAGGGGG CCCAGCTGCC   480
CTGGATCCCT GTGCCTCCGG CCCCTGCCTC AATGGAGGCT CCTGCTCCAA TACCCAGGAC   540
CCCCAGTCCT ATCACTGCAG CTGCCCCCGG GCCTTCACCG GCAAGGACTG CGGCACAGAG   600
AAATGCTTTG ATGAGACCCG CTACGAGTAC CTGGAGGGGG GCGACCGCTG GGCCCGCGTG   660
CGCCAGGGCC ACGTGGAACA GTGCGAGTGC TTCGGGGCC  GGACCTGGTG CGAAGGCACC   720
CGACATACAG CTTGTCTGAG CAGCCCTTGC CTGAACGGGG GCACCTGCCA CCTGATCGTG   780
GCCACCGGGA CCACCGTGTG TGCCTGCCCA CCAGGCTTCG CTGGACGGCT CTGCAACATC   840
GAGCCTGATG AGCGCTGCTT CTTGGGGAAC GGCACTGGGT ACCGTGGCGT GGCCAGCACC   900
TCAGCCTCGG GCCTCAGCTG CCTGGCCTGG AACTCCGATC TGCTCTACCA GGAGCTGCAC   960
GTGGACTCCG TGGGCGCCGC GGCCCTGCTG GGCCTGGGCC CCATGCCTA  CTGCCGGAAT  1020
CCGGACAATG ACGAGAGGCC CTGGTGCTAC GTGGTGAAGG ACAGCGCGCT CTCCTGGGAG  1080
TACTGCCGCC TGGAGGCCTG CGAATCCCTC ACCAGAGTCC AACTGTCACC GGATCTCCTG  1140
GCGACCCTGC CTGAGCCAGC CTCCCCGGGG CGCCAGGCCT GCGGCAGGAG GCACAAGAAG  1200
AGGACGTTCC TGCGGCCACG TATCATCGGC GGCTCCTCCT CGCTGCCCGG CTCGCACCCC  1260
TGGCTGGCCG CCATCTACAT CGGGGACAGC TTCTGCGCCG GAGCCTGGT  CCACACCTGC  1320
TGGGTGGTGT CGGCCGCCCA CTGCTTCTCC CACAGCCCCC CAGGGACAG  CGTCTCCGTG  1380
GTGCTGGGCC AGCACTTCTT CAACCGCACG ACGGACGTGA CGCAGACCTT CGGCATCGAG  1440
AAGTACATCC CGTACACCCT GTACTCGGTG TTCAACCCCA GCGACCACGA CCTCGTCCTG  1500
ATCCGGCTGA AGAAGAAAGG GGACCGCTGT GCCACACGCT CGCAGTTCGT GCAGCCCATC  1560
TGCCTGCCCG AGCCCGGCAG CACCTTCCCC GCAGGACACA AGTGCCAGAT TGCGGGCTGG  1620
GGCCACTTGG ATGAGAACGT GAGCGGCTAC TCCAGCTCCC TGCGGGAGGC CCTGGTCCCC  1680
CTGGTCGCCG ACCACAAGTG CAGCAGCCCT GAGGTCTACG GCGCCGACAT CAGCCCCAAC  1740
```

```
ATGCTCTGTG  CCGGCTACTT  CGACTGCAAG  TCCGACGCCT  GCCAGGGGGA  CTCAGGGGGG  1800
CCCCTGGCCT  GCGAGAAGAA  CGGCGTGGCT  TACCTCTACG  GCATCATCAG  CTGGGGTGAC  1860
GGCTGCGGGC  GGCTCCACAA  GCCGGGGGTC  TACACCCGCG  TGGCCAACTA  TGTGGACTGG  1920
ATCAACGACC  GGATACGGCC  TCCCAGGCGG  CTTGTGGCTC  CCTCCTGACC  CTCCAGCGGG  1980
ACACCCTGGT  TCCCACCATT  CCCTGCCTTG  CTGACAATAA  AGATATTTCC  AAG         2033
```

12. A method of producing a protein having the amino acid sequence of SEQ ID NO: 12, comprising the steps of culturing the transformant according to claim 11, wherein said DNA fragment is ligated at its 5' terminal end to said expression vector by a linker having the nucleotide sequence of SEQ ID NO: 10 to produce a protein having the amino acid sequence of SEQ ID NO: 12 and having at its N-terminal end the amino acid sequence of apolipoprotein E encoded by the linker, and cleaving the N-terminal end amino acid sequence of apolipoprotein E to yield the protein having the sequence according to SEQ ID NO: 12.

* * * * *

UNITED STATES PATENT AND TRADEMARK OFFICE
CERTIFICATE OF CORRECTION

PATENT NO. : 5,466,593
DATED : November 14, 1995
INVENTOR(S) : Takeshi SHIMOMURA et al.

It is certified that error appears in the above-indentified patent and that said Letters Patent is hereby corrected as shown below:

Cover page, item [73]: change "Mitsubishi Kasei Corporation" to --Mitsubishi Chemical Corporation--.

Column 1, line 9: delete "36 kDa";

line 15: after "96", insert --and 34--; change "precursor" to --precursors--;

line 16: change "precursor" to --precursors--;

UNITED STATES PATENT AND TRADEMARK OFFICE
CERTIFICATE OF CORRECTION

PATENT NO. : 5,466,593
DATED : November 14, 1995
INVENTOR(S) : Takeshi Shimomura et al Page 2 of 2

It is certified that error appears in the above-indentified patent and that said Letters Patent is hereby corrected as shown below:

to be continued:

line 17: change "gene" to --genes--;

line 18: change "cursor" to --cursors--.

line 56: delete "having a molecular";

line 57: delete "weight of about 34,000 dalton and".

Column 2, line 11: delete "34,000 dalton".

Signed and Sealed this

Seventeenth Day of June, 1997

Attest:

BRUCE LEHMAN

Attesting Officer

Commissioner of Patents and Trademarks